United States Patent
Bacher

(10) Patent No.: US 6,440,144 B1
(45) Date of Patent: Aug. 27, 2002

(54) MEDICAL INSTRUMENT HAVING A LOCKABLE FORCE TRANSMITTING ELEMENT

(75) Inventor: Uwe Bacher, Tuttlingen (DE)

(73) Assignee: Karl Storz GmbH & Co. KG (DE)

(*) Notice: Subject to any disclaimer, the term of this patent is extended or adjusted under 35 U.S.C. 154(b) by 0 days.

(21) Appl. No.: 09/578,609

(22) Filed: May 25, 2000

(30) Foreign Application Priority Data

Apr. 19, 2000 (DE) .......................... 200 07 177

(51) Int. Cl.$^7$ .............................................. A61B 17/10
(52) U.S. Cl. ....................................... 606/142; 606/208
(58) Field of Search ...................... 606/205, 206–210, 606/142, 143, 144, 148, 149, 150, 151, 169

(56) References Cited

U.S. PATENT DOCUMENTS

| | | | | |
|---|---|---|---|---|
| 2,229,839 A | * | 1/1941 | Crewe | 222/391 |
| D263,635 S | * | 3/1982 | Wendt | D24/24 |
| 4,339,058 A | * | 7/1982 | Wendt | 222/309 |
| 5,413,258 A | * | 5/1995 | Kartler | 222/575 |
| 5,542,949 A | * | 8/1996 | Yoon | 227/901 |
| 5,582,615 A | * | 12/1996 | Foshee et al. | 606/139 |
| 5,755,362 A | * | 5/1998 | Rodriguez et al. | 222/391 |
| 5,792,149 A | * | 8/1998 | Sherts et al. | 606/139 |
| 5,817,111 A | * | 10/1998 | Riza | 112/169 |
| 5,871,488 A | * | 2/1999 | Tovey et al. | 606/139 |
| 5,893,873 A | * | 4/1999 | Rader et al. | 606/205 |
| 5,951,575 A | * | 9/1999 | Bolduc et al. | 606/139 |
| 6,099,550 A | * | 8/2000 | Yoon | 606/205 |

* cited by examiner

Primary Examiner—Michael J. Milano
Assistant Examiner—(Jackie) Tan-Uyen T. Ho
(74) Attorney, Agent, or Firm—St. Onge Steward Johnston & Reens LLC

(57) ABSTRACT

A medical instrument, comprising an elongated shaft having a distal end and a proximal end; a movable tool disposed at said distal end of said shaft; a handle disposed at said proximal end of said shaft; a force transmitting element extending along said shaft and movable in a first and an opposite second movement direction, said force transmitting element being operatively interconnected between said tool and said handle for converting a movement of said handle into a movement of said tool. Steplessly acting locking means coact with said force transmitting element for steplessly locking the movement of said force transmitting element in said first movement direction, whereas said locking means allow free movement of said force transmitting element in said opposite second movement direction.

18 Claims, 3 Drawing Sheets

MEDICAL INSTRUMENT HAVING A LOCKABLE FORCE TRANSMITTING ELEMENT

BACKGROUND OF THE INVENTION

The present invention relates to a medical instrument, comprising:

an elongated shaft having a distal end and a proximate end;

a movable tool disposed at said distal end of said shaft;

a handle disposed at said proximal end of said shaft;

a force transmitting element extending along said shaft and movable in a first and an opposite second movement direction, said force transmitting element being operatively interconnected between said tool and said handle for converting a movement of said handle into a movement of said tool.

An instrument of this kind is known from DE 43 03 544 A1.

This known instrument is an applicator for applying hemostatic clips. Although the present invention is described hereinafter using the example of a clip applicator of this kind, the invention is nevertheless not limited to a medical instrument in the form of such a clip applicator, but rather can also be used with other instruments, as will be described below.

A clip applicator generally has, at the distal end of the shaft, a tool in the form of two jaw parts that are preloaded resiliently into a spread position. The two jaw parts can be pressed together, by advancing a sleeve, out of their spread position into a closed position. The sleeve is joined to an force transmitting element in the form of a push bar that in turn is joined at the proximal end to the movable grip element of the handle of the instrument. The V-shaped or U-shaped clips are arranged in the shaft, serially one behind another, in a magazine. By way of an advance mechanism, the particular clip located closest to the jaw parts is slid between the spreadapart jaw parts. Actuation of the handle moves the force transmitting element (and thus the sleeve) axially in the distal direction, thus pushing the jaw parts together out of their spread position and thereby closing the clip that is located between the jaw parts by deformation.

Clips of this kind are used, for example, to close off blood vessels or for surgical sutures.

When a clip applicator of this kind is used, the problem arises that the clip currently located between the jaw parts can fall out of the jaw parts if, during the operation of closing the jaw parts, the handle is released or the manual force for actuation of the handle is reduced before the clip has been completely closed onto the corresponding tissue or onto the vessel. In particular if the handle is preloaded by spring force into its starting position, the result of releasing the handle during the closing operation would be that the force transmitting element would move back into its starting position; as a result, the jaw parts would open, so that the clip, not yet closed, would fall out of the jaw parts. If a clip is lost in a patient's body, this can have devastating consequences if the loss is not noticed.

This problem cannot be eliminated even if defined click-stop positions, for example by way of a toothed rack, are provided on the handle or the force transmitting element, since the jaw parts can open at least a little way, corresponding to the distance between two click-stop positions, when the handle is released, so that in this instance as well the clip that is located between the jaw parts and is not completely closed can fall out. The surgeon must therefore continuously take care, during the closing operation, not to reduce his manual force on the handle so as not to interrupt the closing operation before the clip is completely closed.

The problem described above occurs, however, not only specifically with a clip applicator but also with other medical instruments in which a movable tool is present that can be moved back and forth in two opposite directions. Such an instrument can, for example, be a forceps for grasping tissue, which has two jaw parts that are closed so as to grasp tissue between the jaw parts for removal from the body. What occurs here is the comparable problem that the jaw parts can open again when the handle is released, so that the tissue being grasped can fall out as the forceps is withdrawn from the body; this must absolutely be avoided as long as the jaw parts are still in the body. Further examples of instruments in which similar problems occur are needle holders and sponge holders.

It is therefore an object of the invention to develop an instrument of the kind cited initially in such a way in the event of a reduction in manual force during actuation of the handle, or in the event the handle is released, the movable tool cannot unintendedly move back opposite to the actuation direction.

SUMMARY OF THE INVENTION

According to the present invention, this object is achieved in the case of the instrument cited initially in that steplessly acting locking means coact with said force transmitting element for steplessly locking the movement of said force transmitting element in said first movement direction, whereas said locking means allow free movement of said force transmitting element in said opposite second movement direction.

Because of the steplessly operating locking means provided according to the present invention, the at least one movable tool can be immobilized in any desired position so as not to move opposite to the actuation direction, while the actuation direction is not impeded. If the handle is released or if there is any reduction in manual force, the tool remains in the position most recently attained. In the case of a clip applicator, because of the stepless locking system the jaw parts cannot unintendedly open again if the handle is released or if there is a reduction in manual force, thus preventing the clip located between the jaw parts from falling out if the clip is not yet applied in completely closed fashion to the vessel or tissue. In the case of a grasping forceps as well, any loss of the grasped tissue inside the body is prevented. The same is true for a needle holder or sponge holder. Because the locking means coact with the force transmitting element, an additional result is an advantageously simple design of the locking mechanism. The force transmitting element remains stationary in any axial position and thus, as soon as the handle is no longer being actuated, also immobilizes the tool in the position it has just reached.

In a preferred embodiment, the locking means are configured so that they coact with the force transmitting element with clamping force in the locked direction.

This feature is advantageous because it makes possible, in a physically simple fashion, a locking system for the movement of the force transmitting element in the locking direction that operates reliably and steplessly, i.e. acts at any desired point in the movement travel of the force transmitting element.

In a further preferred embodiment, the locking means can be brought into engagement with the force transmitting element by spring force.

The advantage here is that the preloading of the locking means by the spring force makes possible reliable automatic engagement with the force transmitting element.

In a further preferred embodiment, means are provided for disengaging the locking means from the force transmitting element in order to move the force transmitting element back in the first movement direction previously locked by the locking means.

The means for disengaging the locking means thus result in cancellation of the locking effect of the locking means, so that the force transmitting element can be moved back into its starting position, after which the instrument is once again ready for the next actuation.

It is particularly preferred in this context if the means for disengaging the locking means are moved along with the force transmitting element, and in a predefined first position coact automatically with the locking means in order to disengage the latter.

It is advantageous in this context that the unlocking of the force transmitting element is also derived automatically from the movement of the force transmitting element, with no need for a manual action in order to unlock the force transmitting element. The predetermined first position at which the means for disengaging the locking means coact with the locking means can advantageously be, for example, the end position of the force transmitting element in which the at least one tool has reached its actuation end position. In conjunction with a clip applicator, this is preferably the position of the force transmitting element in which the jaw parts and thus the clip that is to be applied are completely closed, so that then, by releasing the handle, the force transmitting element can be moved back into the starting position if the handle is correspondingly preloaded by spring force into its starting or rest position.

In this connection, it is further preferred if the means for disengaging the locking means hold the locking means in their non-locking position during the movement of the force transmitting element back in the previously locked first movement direction and, in a predetermined second position, release the locking means so that the locking means can once again coact lockingly with the force transmitting element.

This advantageously ensures that as the force transmitting element is moved back, the locking means are reliably held in their non-locking position, so that the force transmitting element can be moved back into the starting position again in freely movable fashion and without resistance to movement.

Whereas the aforementioned embodiments result in the creation of a generally automatic mechanism for locking, unlocking, relocking, etc. the force transmitting element, it is also preferred if the means for disengaging the locking means are manually actuable.

It is advantageous here that unlocking of the force transmitting element can be performed at any desired movement positions of the force transmitting element between the two axial end positions.

In a further preferred embodiment, the locking means have an axially stationary locking element, at least partially surrounding the force transmitting element circumferentially, that is tiltable into the locking position and vice versa about a pivot axis running eccentrically with respect to the force transmitting element.

This specific embodiment creates a mechanism of advantageously simple design for locking the one movement direction of the force transmitting element, in particular in conjunction with the preloading of the locking means by spring force, by the fact that the locking element, by tilting about the pivot axis running outside the force transmitting element, can be brought into engagement with the latter and out of engagement with it again.

It is further preferred if there is arranged on the locking element, on the side of the force transmitting element located opposite to the pivot axis, a compression spring which tilts the locking element in the direction of the first movement direction to be locked, so that at least one edge of an opening of the locking element comes into clamping contact with the force transmitting element by jamming.

The compression spring provided at this point preloads the locking element against the force transmitting element. Specifically, the compression spring tilts the locking element, with a strong lever effect, in the direction of the locked first movement direction of the force transmitting element, as a result of which the locking element can jam with and thus clamp the force transmitting element. Even if a force is acting on the force transmitting element attempting to move the force transmitting element in the locked movement direction, for example in the case of a spring-loaded handle, any such force even further reinforces the clamping effect between the locking element and the force transmitting element, thus achieving a reliably operating locking action, of immediate onset, on the force transmitting element.

In a further preferred embodiment, the means for disengaging the locking means have a disengagement element that is arranged on the force transmitting element and projects radially beyond it and moves along with the force transmitting element, such that in order to disengage the locking element, in the first position the disengagement element comes into contact against the locking element, as a result of which the latter is tilted out of the tilted locking position into the non-locking position.

This feature creates a disengagement element of simple design for automatic unlocking of the force transmitting element in the aforementioned predetermined first position, with no need for a manual action in order to disengage the locking means.

It is further preferred if the means for disengaging the locking means have a holding element that comes into contact against the locking element after tilting into the non-locking position and holds it in the non-locking position until the force transmitting element has been moved back, opposite to the previously locked movement direction, into the second position.

After the locking element has been tilted into the non-locking position, the holding element assumes the function of the disengagement element when the latter is moved back, along with the force transmitting element, into the starting position. The holding element automatically prevents the locking element from clamping against the force transmitting element, so the latter can be moved in freely movable fashion back into the starting position.

In this context, the holding element has an oblique shoulder onto which the disengagement element runs as the force transmitting element is moved back, thus causing the holding element to move out of contact with the locking element.

The oblique shoulder configured on the holding element, which coacts with the disengagement element as it is moved back into the starting position in order to bring the holding element out of contact with the locking element so that the locking element can once again coact lockingly with the force transmitting element, advantageously results in a mechanism for locking and unlocking the force transmitting element that makes do with few parts, locking and unlocking being brought about solely by the movement of the force transmitting element between the two axial end positions.

In the case of the instrument according to the present invention, provision can advantageously be made either for the force transmitting element to be locked in the proximal movement direction when the force transmitting element is being operated by pushing to actuate the tool, or for the force transmitting element to be locked in the distal movement direction if the force transmitting element is operating by pulling.

As already mentioned, the invention can also be advantageously provided for a forceps, in particular a grasping forceps, for an applicator for applying one or more clips, or for a needle holder or sponge holder.

Further advantages are evident from the description below and the appended drawings.

It is understood that the features recited above and those yet to be explained below can be used not only in the respective combination indicated, but also in other combinations or in isolation, without leaving the context of the present invention.

BRIEF DESCRIPTION OF THE DRAWINGS

An exemplary embodiment of the invention is shown in the drawings and will be explained in more detail with reference thereto in the description below. In the drawings.

DETAILED DESCRIPTION OF A PREFERRED EMBODIMENT

Figures 1, 1A, 1B, 1C:
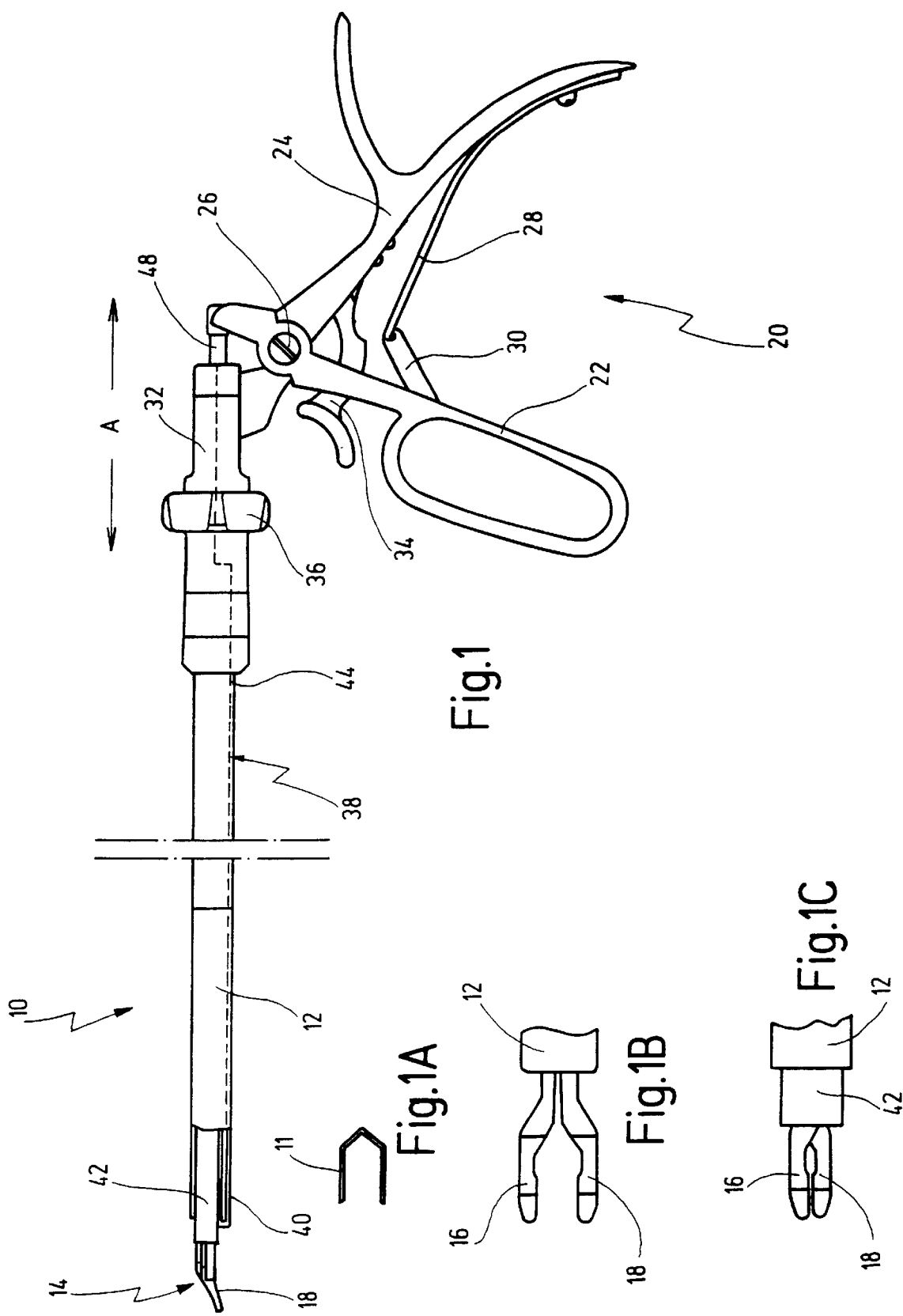
FIG. 1 shows a medical instrument in a discontinuous general representation in a side view, the instrument being configured as an applicator for applying clips.
FIG. 1A shows an individual clip in a plan view.
FIG. 1B shows the distal end of the instrument in FIG. 1 in a plan view and an enlarged representation, in a first operating position.
FIG. 1C shows the distal end of the instrument in FIG. 1B in a second operating position.
Figure 2:
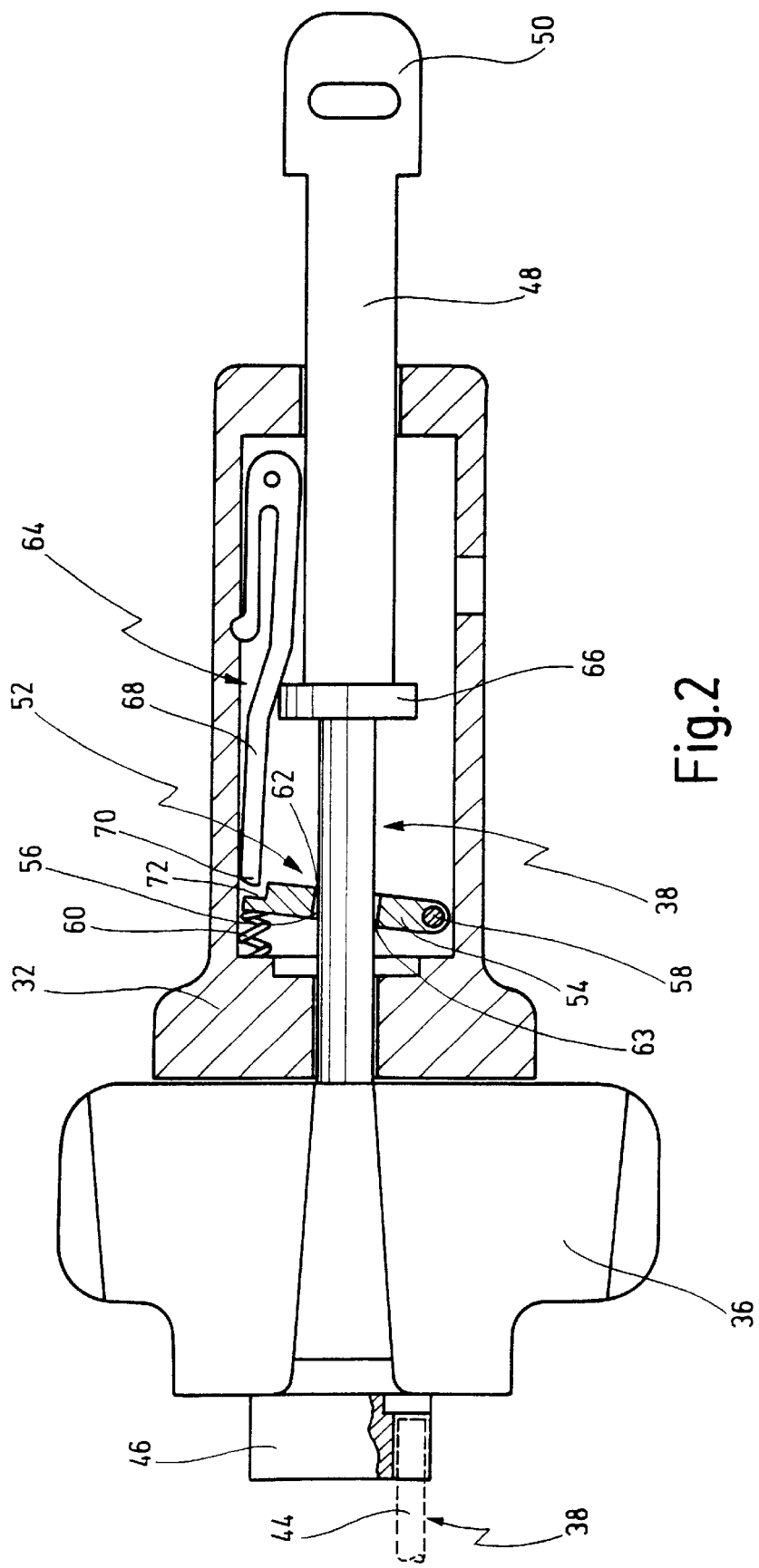
FIG. 2 shows portion A in FIG. 1 at greatly enlarged scale, partially in longitudinal section and in a first operating state, the handle of the instrument having been omitted by comparison with FIG. 1.
Figure 3:
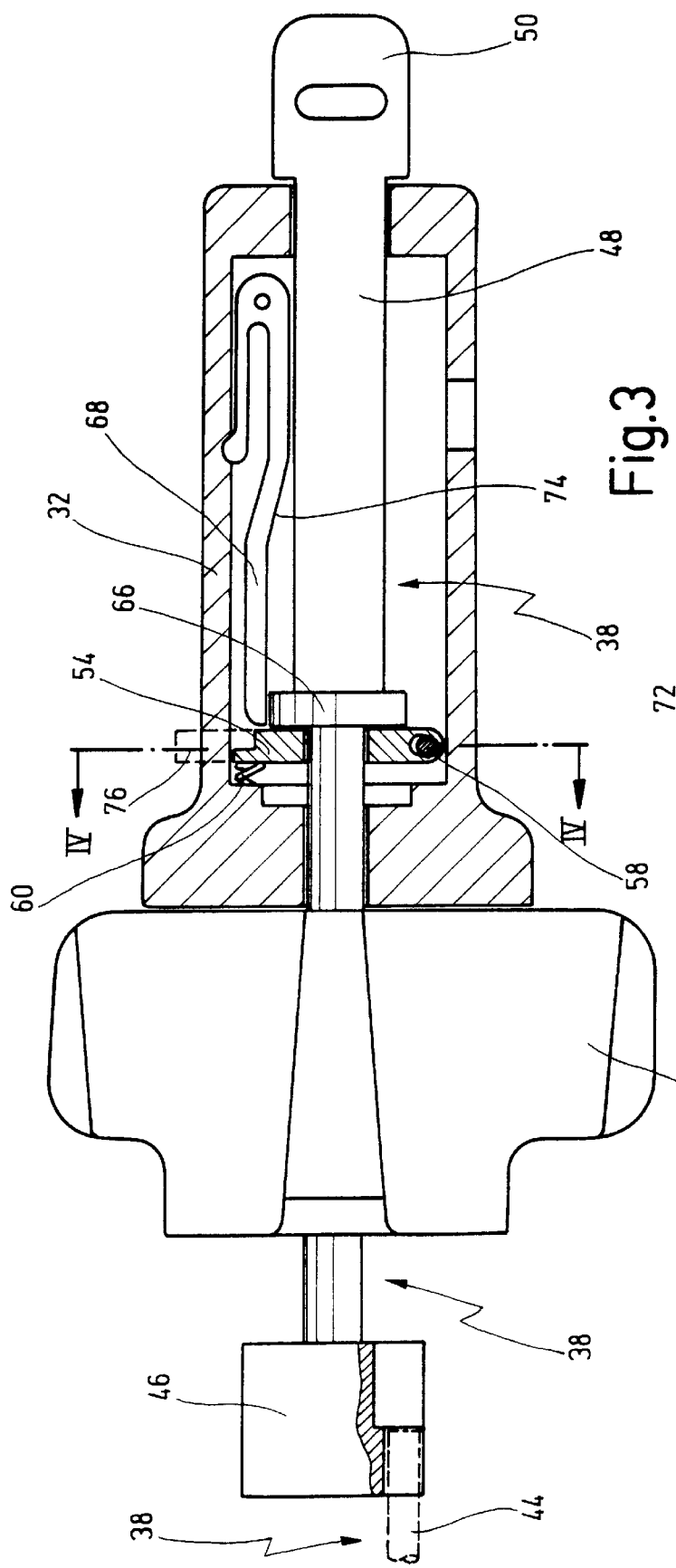
FIG. 3 shows a representation, corresponding to FIG. 2, of the instrument in a second operating state.
Figure 4:
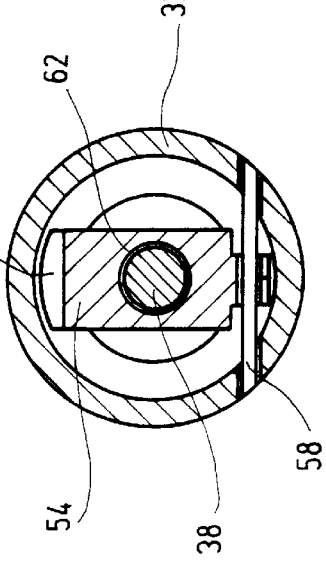
FIG. 4 shows a section along line IV—IV in FIG. 3.

FIG. 1 shows a medical instrument labeled with the general reference character 10, details of which are shown in FIGS. 1B and 1C and in FIGS. 2 through 4.

In the exemplary embodiment shown, instrument 10 is an applicator for applying hemostatic clips. One such clip 11 is shown in isolation, in its original state, in FIG. 1A.

Instrument 10 has an elongated shaft 12 that, in the exemplary embodiment shown, is configured as a tubular shaft.

Arranged at the distal end of shaft 12 is a movable tool 14 that, in accordance with the function of instrument 10 as a clip applicator, has two jaw parts 16 and 18 that are spread resiliently apart from one another. FIG. 1B shows jaw parts 16 and 18 in their spread position, while FIG. 1C shows them in their pressed-together closed position.

Arranged at the proximal end of shaft 12 is a handle 20 that has a movable grip element 22 and a stationary grip element 24. Movable grip element 22 and stationary grip element 24 are joined to one another, pivotably relative to one another, via a rotary joint 26.

Grip elements 22 and 24 are preloaded into their spread position, which is shown in FIG. 1, by way of a pivot lever 30 and a leaf spring 28 that is attached to stationary grip element 24. Grip elements 22 and 24 can be pressed together against the action of leaf spring 28, out of their position shown in FIG. 1, in order to actuate tool 14.

Shaft 12 is joined to stationary grip element 24 via an instrument housing 32.

An interlock 34 is also provided between movable grip element 22 and stationary grip element 24 in order to lock handle 20 in its starting or rest position shown in FIG. 1.

Shaft 12 is furthermore joined to instrument housing 32 rotatably about its longitudinal axis, a rotation ring 36 being provided for rotating shaft 12 about its longitudinal axis.

Inserted between tool 14 in the form of jaw parts 16 and 18 and handle 20 is an force transmitting element 38 that extends along shaft 12 and is movable in the longitudinal direction of shaft 12. In FIG. 1, the greater portion of force transmitting element 38 is schematically indicated with a dashed line. In the region of shaft 12, force transmitting element 38 extends outside the longitudinal center axis of shaft 12. A distal end 40 of force transmitting element 38 is joined immovably to a sleeve 42 that, as shown in FIG. 1C, is partially slidable over jaw parts 16 and 18 in order to move them out of their spread position shown in FIG. 1B into the pressed-together closed position shown in FIG. 1C. Segment 44 of force transmitting element 38 extending through shaft 12 is immovably joined in the region of instrument housing 32 to a block 46 from which force transmitting element 38 extends approximately centeredly through instrument housing 32, a proximal end 48 of force transmitting element 38 having an eye 50 by way of which force transmitting element 38 is joined to movable grip element 22. Proximal end 48 of force transmitting element 38 extending through instrument housing 32 is joined, rotatably about its longitudinal axis, to block 46.

Before the description of instrument 10 is continued, the general function of instrument 10 in terms of applying hemostatic clips will first be described briefly.

The clips, of which one clip 11 is shown in isolation in FIG. 1A, are held in reserve, arranged serially one behind another, in a magazine (not shown in further detail) in shaft 12. By way of an automatic advance mechanism (not shown in further detail), clip 11 located closest to jaw parts 16 and 18 is advanced between jaw parts 16 and 18. Actuating handle 20, i.e. pressing grip elements 22 and 24 together, causes force transmitting element 38 to be pushed in the distal direction, thus pushing sleeve 42, joined immovably to the force transmitting element, over jaw parts 16 and 18, and thereby in turn pressing jaw parts 16 and 18 together, as shown in FIG. 1C. During this closing operation, force transmitting element 38 executes an axial movement stroke of a few millimeters.

In a simple embodiment, however, a clip applicator of this kind can also be configured to receive only one clip at a time, i.e. the particular clip to be applied is then individually placed into instrument 10 before application in the body.

To prevent clip 11 from unintendedly detaching from jaw parts 16 and 18 and becoming lost in the patient's body during the closing operation of jaw parts 16 and 18, by the fact that handle 20 is released or the manual force is decreased, steplessly operating locking means 52 that coact with force transmitting element 38 are provided in instrument 10, as will be described hereinafter in more detail with reference to FIGS. 2 through 4. Locking means 52 allow force transmitting element 38 to move freely in the one movement direction (i.e. in this case in the movement direction from proximal to distal), and in the opposite movement direction (i.e. the movement from distal to proximal) steplessly lock the movement of force transmitting element 38. As a result of the stepless locking of force transmitting element 38, jaw parts 16 and 18 are immobilized, in any desired position between the spread position shown in FIG. 1B and the closed position shown in FIG. 1C, in such a way that they cannot open even slightly out of such a position if handle 20 is released.

Locking means 52 are configured so that they coact clampingly with force transmitting element 38 with frictional engagement.

Locking means 52 have an axially stationary locking element 54 that fits circumferentially at least partially (completely, in the exemplary embodiment shown) around force transmitting element 38. Locking element 54 is embodied in the form of a clamping shackle that has an opening 56 through which force transmitting element 38 passes.

Locking element 54 is furthermore tiltable about a pivot axis 58 extending eccentrically with respect to force transmitting element 38. Pivot axis 58 extends perpendicular to the longitudinal direction of force transmitting element 38. Locking element 54 preferably has vertical play with respect to pivot axis 58, so that locking element 54 rests against force transmitting element 38 at both the top and bottom (in FIG. 2). The extension of locking element 54, or at least opening 56, is moreover correspondingly small in the longitudinal direction of force transmitting element 38, in order to guarantee jamming and clamping.

Arranged on locking element 54 on the side of force transmitting element 38 opposite to pivot axis 58 is a compression spring 60 that is attached to instrument housing 32. The compression spring tilts locking element 54 in the direction of the movement direction to be locked, i.e. in this case in the proximal direction, so that at least one edge 62 of opening 56 of locking element 54 comes into clamping contact with force transmitting element 38. In the exemplary embodiment shown, both proximal edge 62 and a distal edge 63 come into movement-locking contact with force transmitting element 38 by jamming. The locked position of locking element 54 is shown in slightly exaggerated fashion in FIG. 2.

It is understood that because of the arrangement of locking element 54 and compression spring 60 with respect to pivot axis 58, the movement of force transmitting element 38 in the direction from proximal to distal is unrestricted, while the movement of force transmitting element 38 from distal to proximal is locked. When force transmitting element 38 moves from proximal to distal, the clamping effect is cancelled because of the arrangement of locking element 54 and compression spring 60, and force transmitting element 38 can slide through opening 56 in locking element 54. In the case of a pulling force in the proximal direction acting on force transmitting element 38, however, the clamping effect between locking element 54 and force transmitting element 38 is further reinforced, because a pulling force of this kind exerts an additional tilting force on locking element 56 so that the movement of force transmitting element 38 is locked immediately upon application of the pulling force, and it cannot be moved even a short distance in the proximal direction.

Means 64 for disengaging locking means 52 from force transmitting element 38 are also provided in order to allow force transmitting element 38 to be moved back in the movement direction previously locked by locking means 52.

Means 64 for disengaging locking means 52 are present on force transmitting element 38 itself and are moved along with it, and in a predetermined first position coact automatically with locking means 52 to disengage them. Said first position is the position of force transmitting element 38 shown in FIG. 3.

Means 64 for disengaging locking means 52 have a disengagement element 66 that projects radially beyond force transmitting element 38. Disengagement element 66 is configured in the form of a disk that is joined, integrally or as a separate component, to proximal segment 48 of force transmitting element 38. The aforementioned predetermined first position of force transmitting element 38 is precisely the point at which locking element 54 is arranged. As force transmitting element 38 is moved distally, disengagement element 66 comes automatically into contact with locking element 54, causing the latter to be tilted about pivot axis 58 out of its locking position into an upright non-locking position, as shown in FIG. 3.

Means 64 for disengaging locking means 52 retain locking means 52 in their non-locking position during the backward movement of force transmitting element 38 in the previously locked movement direction (i.e. during its movement in the proximal direction).

For that purpose, means 64 have, in order to disengage locking means 52, a resilient holding element 68, configured in the exemplary embodiment shown in the form of a curved leaf spring, that is attached to instrument housing 32. Holding element 68 extends with its distal end as far as locking element 54.

When locking element 54 is in the locking state, as shown in FIG. 2, a distal end 70 of holding element 68 lies in a step-shaped recess 72 at the exposed end of locking element 54.

When locking element 54, as shown in FIG. 3, has been tilted into its non-locking position by coaction with disengagement element 66, distal end 70 of holding element 68 jumps resiliently out of the recess 72 proximally behind locking element 54, as shown in FIG. 3. Force transmitting element 38 can now be moved back in the proximal direction, as a result of which disengagement element 66 once again comes out of contact with locking element 54, but holding element 68 holds locking element 54 in its non-locking upright position.

In a proximal region, holding element 68 has an oblique shoulder 74 with which disengagement element 66 coacts, as force transmitting element 66 moves back in the proximal direction, in order to bring holding element 68 out of contact with locking element 54 once force transmitting element 38 has again reached its starting position, so as to reactivate locking means 52 in the form of locking element 54. The reason is that as release element 66 runs onto oblique shoulder 74, holding element 68 is pushed radially outward so that locking element 54, because of its recess 72, can then once again tilt in the proximal direction in order to lock force transmitting element 38 against any movement in the proximal direction. FIG. 2 shows precisely the state in which holding element 68 has come out of contact with locking element 54. This corresponds to the maximally proximal position of force transmitting element 38. When handle 20 is once again actuated, force transmitting element 38 is again moved distally, so that holding element 68 then moves slightly radially inward in resilient fashion and rests in recess 72 of holding element 68.

The position of force transmitting element 38 shown in FIG. 3 corresponds to its maximally distal position, in which disengagement element 66 has just tilted locking element 54 out of its locking position into its non-locking position.

While the position of force transmitting element 38 shown in FIG. 3 corresponds to the position of jaw parts 16 and 18 in FIG. 1C, the position of force transmitting element 38 in FIG. 2 corresponds to the position of jaw parts 16 and 18 in FIG. 1B.

Instead of the automatic disengagement of locking means 52 as shown in FIG. 3 by the provision of disengagement element 66 and holding element 68, for manual actuation of locking element 54 these two elements can be replaced by configuring locking element 54 so as to project outward through instrument housing 32, for which purpose an opening must be provided in instrument housing 32 at a corresponding point. A segment 76 of locking element 54 protruding out of instrument housing 32 can then be actuated manually in order to unlock locking element 54, by pivoting locking element 54 distally about pivot axis 58.

While force transmitting element 38 operates in pushed fashion in the exemplary embodiment shown, and movement in the proximal direction is locked, it is possible by way of a correspondingly reversed arrangement of locking means 52 described above to lock the distal movement direction of the force transmitting element in the case of an instrument that has an force transmitting element operating in pulled fashion.

It is also understood that the mechanism according to the present invention for locking the movement of the force transmitting element in the one movement direction can be provided not only for the clip applicator set forth in the exemplary embodiment, but also for a grasping forceps, a needle holder, a sponge holder, etc.

What is claimed is:

1. A medical instrument, comprising:
    an elongated shaft having a distal end and a proximal end;
    a movable tool disposed at said distal end of said shaft;
    a handle disposed at said proximal end of said shaft;
    a force transmitting element extending along said shaft and movable in a first and an opposite second movement direction, said force transmitting element being operatively interconnected between said tool and said handle for converting a movement of said handle into a movement of said tool,
    wherein steplessly acting locking means coact with said force transmitting element for steplessly locking the movement of said force transmitting element in said first movement direction, whereas said locking means allow free movement of said force transmitting element in said opposite second movement direction.

2. The instrument of claim 1, wherein said locking means are configured so that they coact with said energy force transmitting element with clamping force in said locked first movement direction.

3. The instrument of claim 1, wherein said locking means can be brought into engagement with said force transmitting element by spring force.

4. The instrument of claim 1, wherein means are provided for disengaging said locking means from said force transmitting element in order to move said force transmitting element back in said first movement direction previously locked by said locking means.

5. The instrument of claim 4, wherein said means for disengaging said locking means are moved along with said force transmitting element, and in a predefined first position thereof coact automatically with said locking means in order to disengage the latter.

6. The instrument of claim 5, wherein said means for disengaging said locking means hold said locking means in their non-locking position during the movement of said force transmitting element back in the previously locked first movement direction and, in a predetermined second position, release said locking means so that said locking means can once again coact lockingly with said force transmitting element.

7. The instrument of claim 1, wherein means are provided for disengaging said locking means from said force transmitting element in order to move said force transmitting element back in said first movement direction previously locked by said locking means and wherein said means for disengaging the locking means are manually actuable.

8. The instrument of claim 1, wherein said locking means have an axially stationary locking element, at least partially surrounding the force transmitting element circumferentially, that is tiltable into its locking position and vice versa about a pivot axis running eccentrically with respect to said force transmitting element.

9. The instrument of claim 8, wherein there is arranged on said locking element, on the side of said force transmitting element located opposite to said pivot axis, a compression spring which tilts said locking element in the direction of said first movement direction to be locked, so that at least one edge of an opening of said locking element comes into clamping contact with said force transmitting element by jamming with said force transmitting element.

10. The instrument of claim 1, wherein means are provided for disengaging said locking means from said force transmitting element in order to move said force transmitting element back in said first movement direction previously locked by said locking means, and wherein said locking means have an axially stationary locking element, at least partially surrounding the force transmitting element circumferentially, that is tiltable into its locking position and vice versa about a pivot axis running eccentrically with respect to said force transmitting element and, wherein said means for disengaging said locking means have a disengagement element that is arranged on said force transmitting element and projects radially beyond it and moves along with said force transmitting element, such that in order to disengage said locking element, in said first position said disengagement element comes into contact against said locking element, as a result of which the latter is tilted out of the tilted locking position into a non-locking position.

11. The instrument of claim 10, wherein said means for disengaging said locking means have a resilient holding element that comes into contact against said locking element after tilting into the non-locking position and holds it in the non-locking position until said force transmitting element has been moved back, opposite to said previously locked-first movement direction, into said second position.

12. The instrument of claim 11, wherein said holding element has an oblique shoulder onto which said disengagement element runs as said force transmitting element is moved back, thus causing said holding element to move out of contact with said locking element.

13. The instrument of claim 1, wherein said force transmitting element is locked in proximal movement direction as said first movement direction.

14. The instrument of claim 1, wherein said force transmitting element is locked in the distal movement direction as said first movement direction.

15. The instrument of claim 1, wherein it is a forceps, in particular a grasping forceps.

16. The instrument of claim 1, wherein it is an applicator for applying at least one clip.

17. The instrument of claim 1, wherein it is a needle holder.

18. The instrument of claim 1, wherein it is a sponge holder.

* * * * *